United States Patent [19]

Masreliez

[11] Patent Number: 5,759,159
[45] Date of Patent: Jun. 2, 1998

[54] METHOD AND APPARATUS FOR APICAL DETECTION WITH COMPLEX IMPEDANCE MEASUREMENT

[75] Inventor: C. Johan Masreliez, Redmond, Wash.

[73] Assignee: Ormco Corporation, Glendora, Calif.

[21] Appl. No.: 719,333

[22] Filed: Sep. 25, 1996

[51] Int. Cl.⁶ .................................................. A61B 5/05
[52] U.S. Cl. ................................... 600/547; 600/590
[58] Field of Search .......................... 128/734, 779; 33/27, 32; 600/547, 590

[56] References Cited

U.S. PATENT DOCUMENTS

| | | | |
|---|---|---|---|
| 3,901,216 | 8/1975 | Felger | 128/2.1 Z |
| 4,193,408 | 3/1980 | Fujino | 128/734 |
| 4,353,693 | 10/1982 | Déry et al. | 433/27 |
| 4,447,206 | 5/1984 | Ushiyama | 433/27 |
| 4,526,179 | 7/1985 | Salesky | 128/776 |
| 5,017,134 | 5/1991 | Saito et al. | 433/72 |
| 5,020,541 | 6/1991 | Marriott | 128/734 X |
| 5,063,937 | 11/1991 | Ezenwa et al. | 128/734 X |
| 5,080,586 | 1/1992 | Kawai | 433/32 |
| 5,096,419 | 3/1992 | Kobayashi et al. | 433/72 |
| 5,112,224 | 5/1992 | Shirota | 433/27 |
| 5,211,556 | 5/1993 | Kobayashi et al. | 433/72 |
| 5,295,833 | 3/1994 | Chihiro et al. | 433/224 |

*Primary Examiner*—Francis Jaworski
*Attorney, Agent, or Firm*—Wood, Herron & Evans, L.L.P.

[57] ABSTRACT

An apical position detector for use in dental endodontics includes an electronic controller coupled to a conductive probe and a lip electrode. The probe is positioned in a root canal and the lip electrode contacts another location on the patient's body. The controller produces a test signal as a combination of signals at selected frequencies. The controller then monitors a voltage of the probe and extracts the amplitude and phase of each of the frequency components of the voltage at the probe. Test scores are generated from summations of the amplitudes and/or phases of the various frequency components to determine when the impedance between the probe and the lip electrode changes from a primarily reactive impedance to a primarily resistive impedance. A first test score is displayed to indicate when the impedance changes from a reactive to a resistive impedance. The second test score indicates when the measurement conditions are unsatisfactory. The test scores are displayed in bar graph or similar form.

32 Claims, 4 Drawing Sheets

METHOD AND APPARATUS FOR APICAL DETECTION WITH COMPLEX IMPEDANCE MEASUREMENT

TECHNICAL FIELD

The present invention relates to dental equipment, and more particularly, to measuring equipment for dental endodontics.

BACKGROUND OF THE INVENTION

In root canal therapy, the root canal, which is a passageway through a tooth, is cleaned of undesired material, such as tissue and fluid. To clean the canal, a dental tool, such as a drill or file, is inserted into the canal and manipulated to remove the undesired material. Then, a flexible filler substance is placed in the root canal and the canal is sealed with a rigid material.

It is sometimes difficult to determine whether the root canal has been cleaned to the proper depth because the narrow root canal does not provide a clear viewing path and medical fluids can partially fill the canal, obscuring vision. A particularly troublesome area is at the apex of the root canal, or apical foramen, where the root canal ends and the patient's tissue begins. If the canal is not completely cleaned, debris left inside the canal can prevent proper healing. Therefore, the dental tool should be inserted to the apex of the root canal during cleaning to remove all debris. However, if the dental tool is inserted too deeply, the tool penetrates the tissue, causing swelling and unnecessary trauma for the patient. It is therefore beneficial to identify the apical position of the root canal so that the root canal can be cleaned fully, without excessive trauma to the patient.

In one method of determining the apical position, a metal file is inserted into the canal and the tooth is x-rayed. In the x-ray image, the metal file contrasts with the surrounding tooth and body tissue so that the file position can be compared to the apical position. This method can be very unreliable, costly, and time-consuming. Moreover, where the tooth is behind a cheekbone, an x-ray will not provide a proper image.

U.S. Pat. No. 5,211,556 to Kobayashi et al. describes an electronic approach to determining the apical position where a conductive probe is inserted into the root canal and an electrode is positioned in contact with the patient's body, in or near the mouth. Then, the probe is moved through the root canal toward the base of the tooth. As the probe is moved, the magnitude of the impedance, or a component thereof, is monitored. When the probe approaches the apex of the root canal, the magnitude of the impedance begins to change at a different rate. The detector determines that the probe is at the apex of the root canal when the impedance is within a designated range. However, the impedance may be affected significantly by the presence of medical liquids or other material in and around the root canal. For example, the medical liquids can be conductive, thereby reducing the impedance between the electrodes, as compared to a dry root canal. Consequently, the above-described system is subject to errors in measurement of the apical position. Further, this approach typically requires calibration of the detector during each measurement procedure due to the variations in the amount of medical fluids and other materials in the mouth.

In an attempt to reduce the above-described problems, U.S. Pat. No. 5,096,419 to Kobayashi et al., describes an approach to apical detection where measurements of impedance are taken at a plurality of frequencies. Then, the apical position is determined by calculating a ratio of impedances at two different frequencies. Environmental conditions, such as medical liquids, can still detrimentally affect such measurements. Additionally, the use of a ratio inherently limits the approach to making measurements at two, and only two, frequencies.

SUMMARY OF THE INVENTION

An apex finder or apical position detector determines apical position by detecting a phase angle, reactive component or spectral response of an impedance between a pair of electrodes. A conductive probe inserted into a root canal forms the first electrode. The second electrode contacts the patient's body, typically in the mouth area.

In one embodiment, the apical detector uses a sum of a plurality of phase angles where the phase angles are determined at separate frequencies. The phase angles change significantly when the probe contacts the patient's body tissue. By using a combination of measurements at a plurality of frequencies, the apical position detector provides a more accurate indication of the apical position.

In one embodiment, the apical detector also uses a combination of the amplitudes of the impedances in addition to the summation of the phase angles, to improve the accuracy of the apical detector. The phase angles and magnitudes are combined mathematically to form a first test score. When the first test score is within a designated range, the position detector indicates that the probe is at the apex of the root canal. The apical detector averages the magnitudes of the impedances at the testing frequencies to indicate whether the conductivity of the root canal is too high. The apical position detector also produces a second test score based upon the magnitudes to indicate to a user unfavorable measurement conditions in the root canal.

A display panel presents both test scores with bar graphs to provide an easily recognizable visual indication of the apical position. Additionally, the display panel includes a warning light to provide a prominent indication of unfavorable measurement conditions. To provide even further information, a chime or other acoustic indicator sounds to indicate that the probe has reached the apex of the root canal.

In a method according to the invention, the apical position detector includes a microprocessor-based controller. The controller uses a Fast-Fourier Transform ("FFT") approach to determine the components of the impedance. The controller develops the test score based upon a sum of phase angles to indicate the position of the probe relative to the apex of the root canal.

In another method according to a preferred embodiment of the invention, the electrodes are driven with a pulsed signal. The controller then compares a spectral response or pulse time delay to a reference standard to identify the apical position.

DETAILED DESCRIPTION OF THE INVENTION

Figure 1:
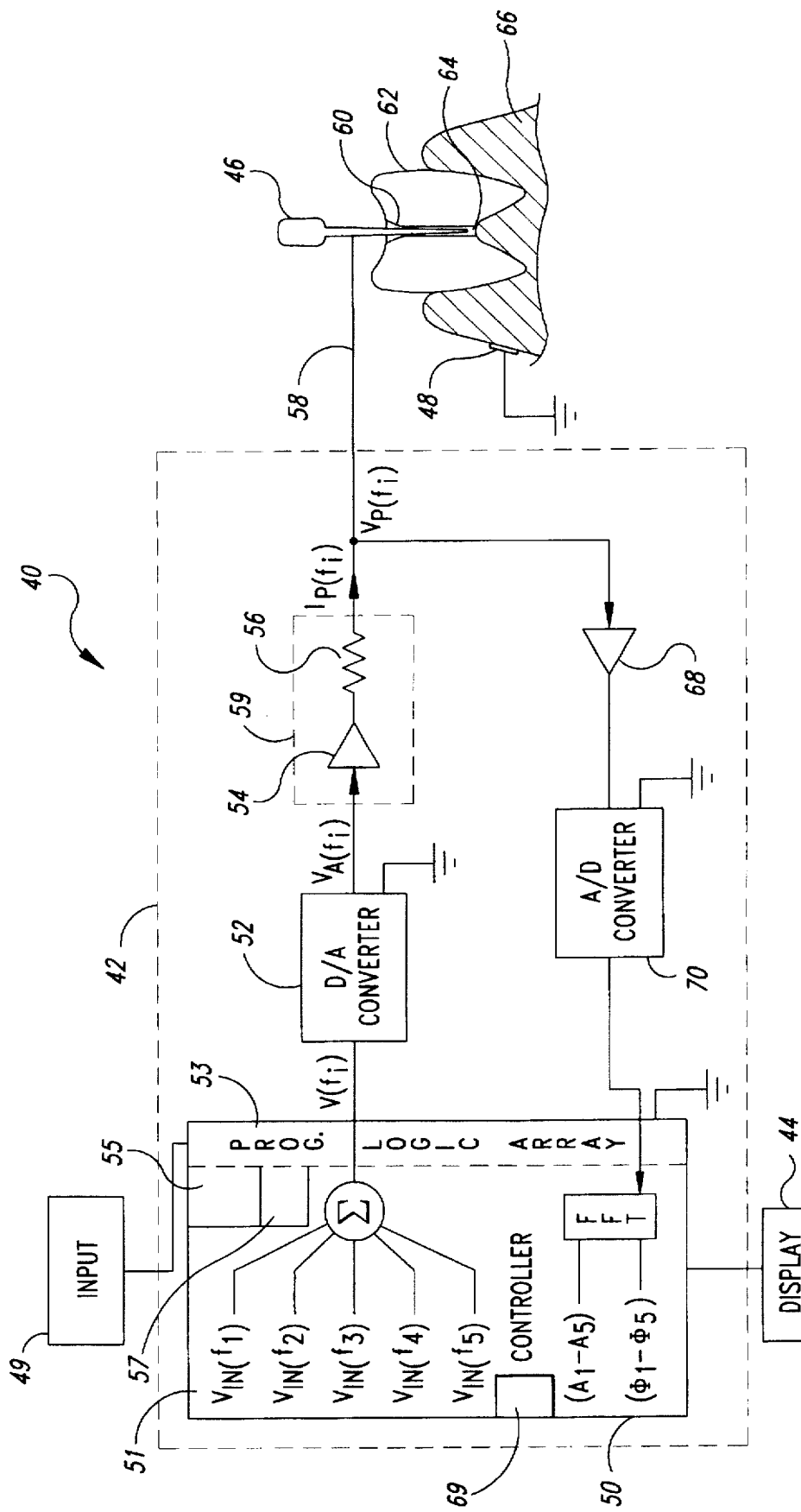
FIG. 1 is a diagrammatic representation of an apical position detector according to the invention with a probe positioned in a root canal.

As shown in FIG. 1, an apical position detector 40 includes a control circuit 42, a display 44, a conductive canal probe 46, a lip electrode 48 and an input interface 49. A microprocessor-based controller 50 within the control circuit 42 controls operation of the position detector 40 in response to a software program stored in a nonvolatile program memory 55 as will be described below. The input interface 49 includes a switch panel, keyboard, or similar device that allows a user to activate the position detector 40, select options, adjust sensitivity and otherwise control the position detector 40.

In addition to a microprocessor 51, the controller 50 also includes a programmable gate array 53 that acts as an interface between the microprocessor 51 and the remainder of the control circuit 42. The programmable gate array 53 also includes a latching circuit that latches commands from the switch panel, keyboard or other device for use in an interrupt handler routine described below with respect to FIG. 3B. Additionally, a nonvolatile programmable read-only memory 57 in the controller 50 contains a table of predetermined voltage levels that are accessed by the microprocessor 51 at selected time intervals to produce a digital multi-frequency testing signal $V(f_i)$ that provides the principal testing signal for the control circuit 42. Preferably, the testing signal $V(f_i)$ has components at five frequencies $f_1-f_5$. The frequencies are preferably in the range of 200 Hz to 10 kHz, although frequencies exceeding 50 kHz may be within the scope of the invention. In one embodiment, the frequencies $f_1-f_5$ are 500 Hz, 1 kHz, 2 kHz, 4 kHz, and 8 kHz, respectively. Each of the frequencies $f_2-f_5$ is double that of the next lower frequency $f_1-f_4$ to simplify a Fast-Fourier Transform computation described below.

The testing signal $V(f_i)$ from the controller 50 drives a digital-to-analog (D/A) converter 52. In response, the D/A converter 52 produces an analog testing signal $V_A(f_i)$. The analog testing signal $V_A(f_i)$, in turn, provides input to a series combination of a buffer amplifier 54 and a test resistor 56 to produce a current $I_P(f_i)$ for driving the probe 46. The test resistor 56 has a resistance on the order of 200 kΩ that makes the series combination of the buffer amplifier 54 and test resistor 56 act substantially as a current source 59, such that the probe current $I_P(f_i)$ is substantially constant.

The probe current $I_P(f_i)$ is coupled from the test resistor 56 to the probe 46 through a cable 58 that is sufficiently long and flexible to allow easy manipulation of the probe 46. The probe current $I_P(f_i)$ travels from the cable 58 through the conductive shaft of the probe 46 into a root canal 60 of a tooth 62. Then, the current $I_P(f_i)$ travels from the distal end of the probe 46 through an end region 64 of the root canal 60 and into a patient's body tissue 66 to the grounded lip electrode 48 to ground. The length of the end region 64 will depend upon the depth to which the probe 46 is inserted into the root canal 60.

The end region 64 and the body tissue 66 form a conductive path having an impedance Z between the probe 46 and the lip electrode 48. As is known, the impedance Z can be modeled adequately as a parallel combination of a resistor and a capacitor as shown in the equivalent circuit of FIG. 2. The probe current $I_P(f_i)$ flows through the impedance Z and produces a node voltage $V_P(f_i)$ that equals the current $I_P(f_i)$ times the impedance Z. The node voltage $V_P(f_i)$ will then vary according to the impedance Z, because the current $I_P(f_i)$ is substantially constant. When the distal end of the probe 46 first enters the root canal 60 (FIG. 1), the impedance Z is high and has a large resistive component. Therefore, the node voltage $V_P(f_i)$ is large and has little or no phase shift relative to the current $I_P(f_i)$. As the distal end of the probe 46 approaches the body tissue 66, the impedance Z falls and becomes more capacitive. Consequently, the node voltage $V_P(f_i)$ falls and has an increasing phase shift with respect to the current $I_P(f_i)$.

Figure 2:
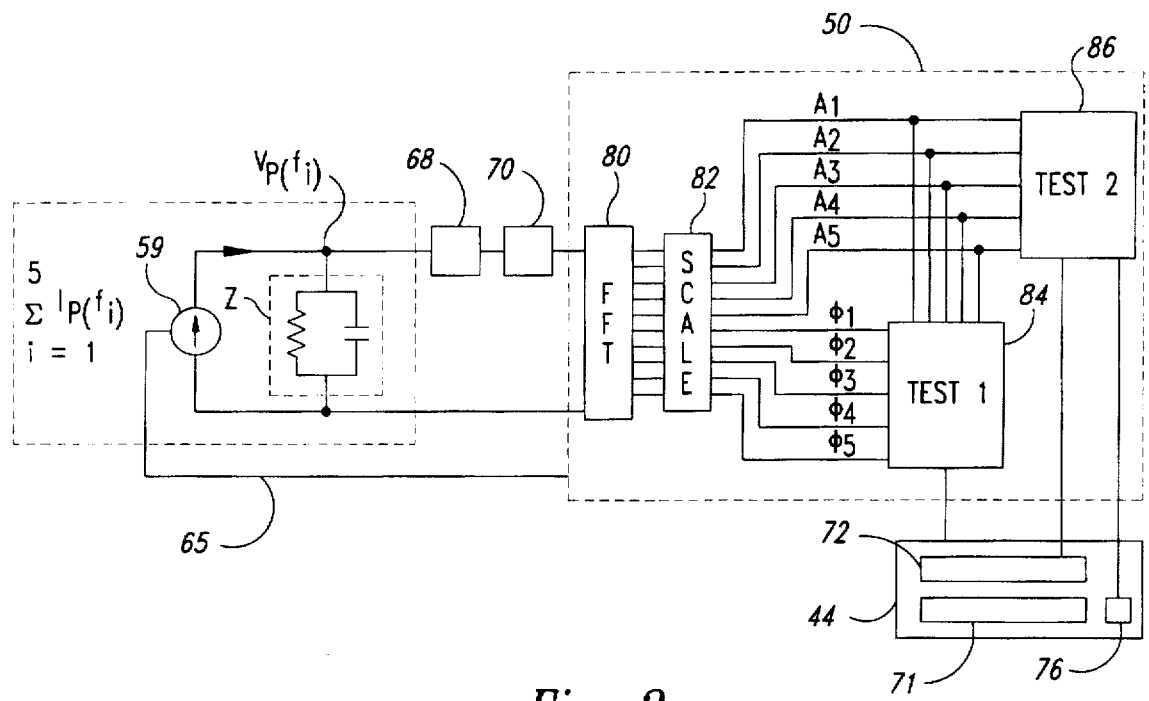
FIG. 2 is a partial circuit model and partial block diagram of the apical position detector and root canal of FIG. 1.

The controller 50 resolves the phase angles $\varnothing_1-\varnothing_5$ and amplitudes $A_1-A_5$ of the various components of the node voltage $V_P(f_i)$ through a Fast-Fourier Transform technique, as represented by an FFT block 80 in FIG. 2. The controller 50 then scales the components $A1-A5$, $\varnothing_1-\varnothing_5$ as represented by a scale block 82 to produce a set of normalized components. From the normalized phase angles $\varnothing_1-\varnothing_5$ and amplitudes $A_1-A_5$ the controller 50 produces test scores TEST1 and TEST2 as represented by the score blocks 84, 86. Based upon the test scores TEST1, TEST2, the controller 50 provides information to a user through the display 44.

Figure 3A:
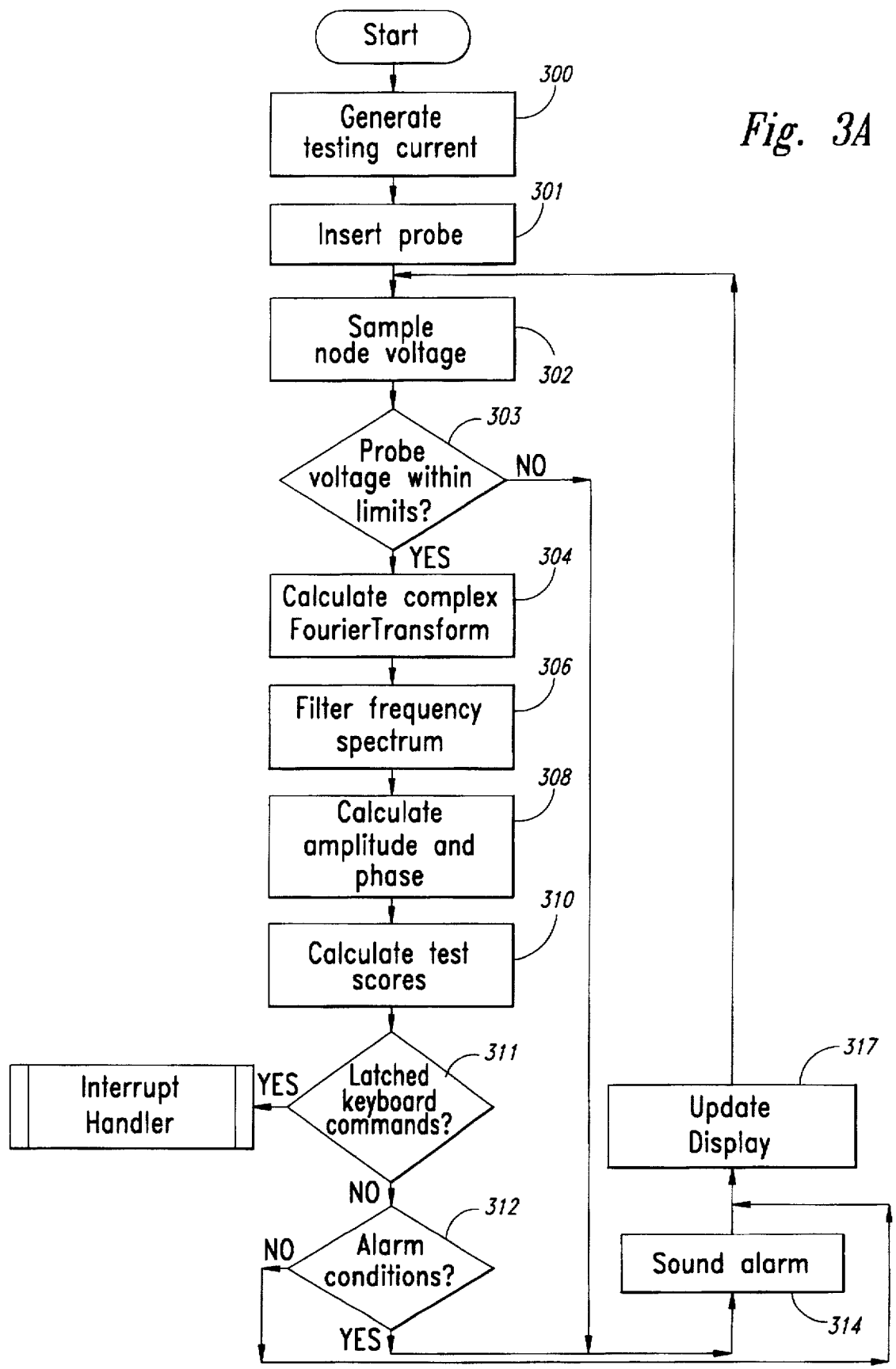
FIG. 3A is a firmware flow chart showing the steps for detecting apical position and the signal display and control paths of the position detector of FIG. 1.
Figure 3B:
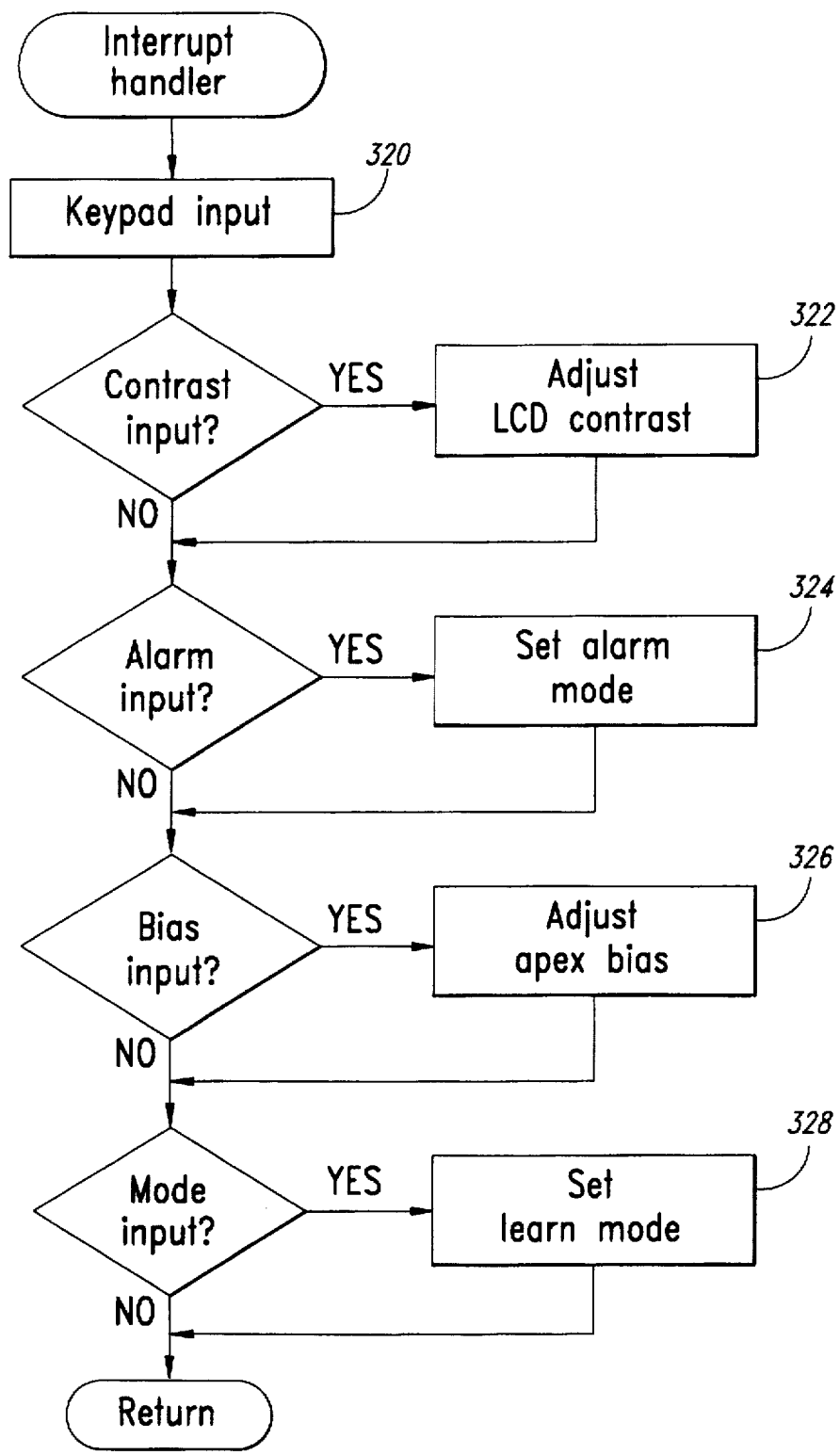
FIG. 3B is a flowchart of an interrupt handler routine showing steps for user input to the detector of FIG. 1.

The steps for detecting apical position are shown in greater detail in the firmware flow chart of FIGS. 3A and 3B. It is assumed for purposes of this description that the nonvolatile read-only memory 57 has already been programmed to establish the desired voltage levels described above. As shown in FIG. 3A, position detection begins in step 300 with generation of the probe current $I_P(f_i)$ with five frequency components. The probe current $I_P(f_i)$ is then applied by insertion of the probe 46 in step 301. Next, in step 302, the control circuit 42 monitors the node voltage $V_P(f_i)$ through a buffer amplifier 68 and an analog-to-digital (A/D) converter 70 (FIG. 1). The A/D converter 70 provides to the controller 50 a digital signal representing the node voltage $V_P(f_i)$.

In step 303, the controller 50 evaluates the node voltage $V_P(f_i)$ to detect a node voltage $V_P(f_i)$ above at maximum level. If the node voltage $V_P(f_i)$ is excessive, the controller 50 determines that the probe 46 is not in or near contact with the patient and the warning light 76 is then activated to provide a substantially instantaneous indication of a non-measuring situation. The controller 50 also freezes the display 44 to hold the last detected measurement.

Next, in step 304, software within the controller 50 performs a Fast-Fourier Transform (FFT) on the digital signal from the A/D converter 70, as represented by the block FFT in FIGS. 1 and 2, to produce a frequency spectrum. The spectral components are then filtered to remove noise and A/D converter quantizing errors in step 306 and the spectrum is manipulated mathematically to produce the amplitudes $A_i$ and phases $\varnothing_i$ of the five frequency components in step 308. The amplitudes $A_i$ and phases $\varnothing_i$ are stored in a memory 69 in the controller 50 for use in calculations. Then, in step 310, the software normalizes the amplitudes $A_i$ and phases $\phi_i$ to produce a test score TEST1 according to the formula:

$$\text{TEST1} = [\{3*(A_1/A_2)*(A_1/A_3)*(A_1/A_4)*(A_1/A_5)\} - \{(-\phi_1 - \phi_2 - \phi_3 - \phi_4)/4\}]/36,$$

$$= AMP1 - PHI$$

where AMP1 will be referred to herein as the amplitude component of the first test score TEST1 and PHI will be referred to as the phase component of the first test score TEST1.

Also in step 310, the software determines a second test score TEST2 according to the formula:

$$\text{TEST 2} = 5,000/(A_1+A_2+A_3+A_4+A_5)$$

When the distal end of the probe 46 contacts the body tissue 66, the magnitude of the impedance Z, and thus the node voltage $V_p(f_i)$, drops quickly for all of the frequency components. However, the amplitude component AMP1 of the first test score TEST1 varies much less rapidly than the magnitudes $A_1$–$A_5$, because each of the components is normalized to the first component $A_1$. Consequently, changes in the magnitudes $A_2$–$A_5$ of the node voltage $V_p(f_i)$ will be offset by changes in the magnitude $A_1$ for the first frequency. The amplitude component AMP1 will thus vary only to the extent that the rates of change of the amplitudes $A_1$, $A_2$–$A_5$ differ.

The phase component PHI of the first test score TEST1 is largely a function of the relative magnitudes of the reactive and resistive components of the impedance Z. Thus, when the impedance Z is substantially resistive, the phase component of the first test score TEST1 will be substantially zero. When the impedance Z is substantially reactive, the phase component of the first test score TEST1 will be at its maximum. As noted above, the impedance Z changes from being substantially resistive to substantially reactive as the probe 46 nears contact with the body tissue 66. Therefore, the phase component PHI of the first test score TEST1 will change from substantially zero to its maximum magnitude as the probe 46 approaches contact with the body tissue 66.

The second test score TEST2 will rise quickly as the probe 46 reaches the body tissue 66, because the second test score TEST2 is inversely proportional to the amplitudes $A_1$–$A_5$ and the amplitudes $A_1$–$A_5$ drop as the probe 46 reaches the apical position. The second test score TEST2 can therefore be used to confirm the results of the first test score TEST1. Also, the second test score TEST2 can indicate whether the magnitude of the impedance Z is within an acceptable range. An excessively low impedance magnitude can indicate unfavorable measurement conditions, such as may result from excessive medical fluids around the probe 46. An excessively high impedance magnitude can indicate that the probe 46 is not yet inserted, and can be used to interrupt the software routine as a supplement to step 303 described above. Once the test scores are calculated, the software in step 311 polls to see if the programmable gate array 53 has latched any commands from the input interface 49. If no commands have been latched, the software compares the first or second test scores, TEST1, TEST2 to an acceptable range to identify either contact with the body tissue or unfavorable measurement conditions. A warning light 76 alarm or other indicator is activated in step 314 if the test scores TEST1, TEST2 are outside of the acceptable range.

Figure 4:
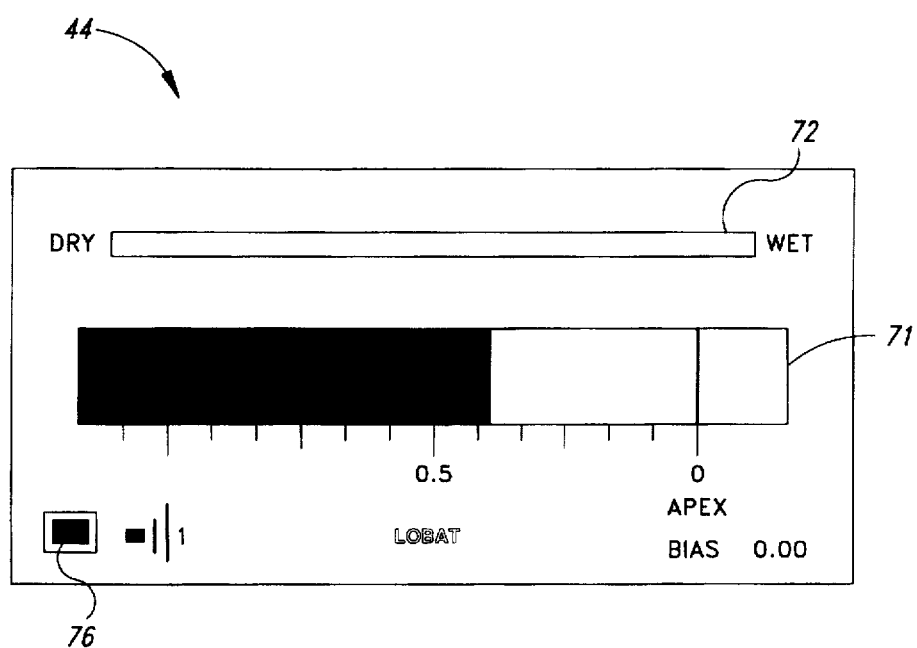
FIG. 4 is a front elevational view of the display of FIG. 1, showing a broad bar graph, a narrow bar graph and a warning light.

Next, the first test score TEST1 is displayed (step 317) on the display 44 as a broad bar graph 71, as shown in FIG. 4. The broad bar graph 71 provides a prominent graphical indication of when the distal end of the probe 46 contacts the tissue 66. The second test score TEST2 is also provided on the display as a narrow bar graph 72 to indicate whether the impedance Z is within a range that provides adequate results. Alternatively, the first and second test scores TEST1, TEST2 can be presented numerically by a seven-segment display or any other suitable indicating device.

If, in step 311, a user has input a command through the input interface 49, the software jumps to an interrupt handler routine as shown in FIG. 3B. As shown in step 320, during the interrupt period, the software accepts latched inputs from the input interface 49 (FIGS. 1 and 2) to adjust the display contrast (step 322), select alarm mode (step 324), adjust sensitivity of apex bias level (step 326), or place the controller 50 in a learning mode (step 328). Once the interrupt handler routine is complete, the software returns to step 312 to evaluate alarm conditions and display the results.

While the present invention has been described herein by way of exemplary embodiment, various modifications may be made without departing from the spirit and scope of the invention. For example, the embodiment of FIG. 1 utilizes a test signal $V(f_i)$ having five principal frequency components, although fewer or more frequency components can be used. Alternatively, a variety of other spectral or phase analysis techniques can be used to identify the apical position. For example, the test signal $V_p(f_i)$ can be a short pulse, thereby providing an input having a broad spectral content. Then, the overall spectral content of the node voltage $V_p(f_i)$ can be monitored and compared to a reference spectral response to determine the apical position. Using the same type of input pulse, the shape of the pulse response at the node can be monitored and compared to a reference pulse response to determine the apical position. As another alternative, one or more pulses can be input and the time delay of output pulses can be detected. The time delay can indicate the apical position because the time delay corresponds to the capacitive component of the impedance Z.

Similarly, the digital version of the test signal $V(f_i)$ can be resolved using a variety of techniques other than the Fast-Fourier Transform technique. For example, a heterodyning circuit or other frequency resolving approach can be applied to extract the phases and amplitudes of the various frequency components. Additionally, while the test scores described herein use specific algorithms for normalizing amplitudes and summing the various components, a variety of other algorithms may be within the scope of the invention. For example, the phase component PHI or another mathematical function of the phases $\emptyset_i$–$\emptyset_5$ can be used to provide a separate indicator of contact between the probe 46 and the tissue 66. Likewise, each of phases $\emptyset_i$–$\emptyset_5$ may be presented separately or a variety of other combinations of the phases and amplitude can be used to provide the indication of contact between the probe 46 and tissue 66. Moreover, the display 44 principally uses a pair of bar graphs to indicate the test scores TEST1, TEST2. Alternatively, the test scores TEST1, TEST2 may be presented by way of a variety of other display techniques, including numerical indicators, colored lights, or any of a variety of other display techniques. Further, the first test score TEST1 can be used to activate a chime, beeper, or other audible indication of contact with the tissue 66. Also, a chime or other indicator can be used to indicate unacceptable measurement conditions in place of or as a complement to the warning light 76 described above. Accordingly, the invention is not limited except as by the appended claims.

I claim:

1. An apical detection apparatus, comprising:

a first electrode, the first electrode including a conductive probe shaped for penetrating a root canal of a tooth;

a second electrode configured to electrically contact a patient's body;

a phase detector coupled to the first and second electrodes, the phase detector being operative to detect a phase of a complex impedance having a real component and a reactive component;

a user interface coupled to the phase detector to provide an indication to a user of a parameter that is a function of the detected phase;

an electronic controller coupled to the phase detector, the controller being operative to produce a signal indicating location of the probe at an apex of the root canal as a function of the detected phase; and an amplitude detector operative to detect the magnitude of the complex impedance, wherein the controller is operative to produce the signal indicating location of the probe at an apex of the root canal as a function of both the detected phase and the magnitude.

2. An apical detection apparatus, comprising:

a first electrode, the first electrode including a conductive probe shaped for penetrating a root canal of a tooth;

a second electrode configured to electrically contact a patient's body;

a phase detector coupled to the first and second electrodes, the phase detector being operative to detect a phase of a complex impedance having a real component and a reactive component;

a user interface coupled to the phase detector to provide an indication to a user of a parameter that is a function of the detected phase; and a signal source coupled to the first and second electrodes, the signal source providing a testing signal to the first and second electrodes, the testing signal including a plurality of test frequencies, wherein the phase detector is operative to detect the phase of the complex impedance at each of the test frequencies.

3. The apical detector of claim 2, further including an electronic controller coupled to the phase detector, the controller being operative to produce a signal indicating location of the probe at an apex of the root canal as a cumulative function of the phases at the test frequencies.

4. An apparatus for detecting contact with a body tissue of a first type in a patient, comprising:

a first electrode coupleable to the patient's body;

a second electrode movable to contact the tissue of the first type, the second electrode including a probing member for contacting the patient's body; and a complex impedance sensor coupled to the first and second electrodes and configured to detect a plurality of amplitude relationships among at least three different frequencies and a plurality of relationships between real and reactive components of impedances at at least three different frequencies between the first and second electrodes.

5. The apparatus of claim 4 wherein the complex impedance sensor includes:

a signal source producing a first testing signal at a first frequency, a second testing signal at a second frequency and a third testing signal at a third frequency, the signal source being coupled to the first or second electrodes to provide the first second and third testing signals to the patient; and a signal monitor coupled to first or second electrode and detecting a plurality of relative phases of current and voltage in response to the first, second and third testing signals.

6. The apparatus of claim 4 further including a memory device coupled to the complex impedance sensor and configured to store information representing a plurality of relationships between the real and reactive components at the first, second and third frequencies.

7. The apparatus of claim 6 wherein the complex impedance sensor includes a signal monitor coupled to the first or the second electrode and means for detecting relative phases of current and voltage in response to the first, second and third testing signals, wherein the information representing the real and reactive components includes the relative phases of the current and voltage at the first, second and third frequencies.

8. A method of detecting an apical location in a root canal of a patient comprising the steps of:

electrically coupling to the patient at a first location;

probing the root canal at a second location;

detecting a complex impedance between the first location and the second location, the complex impedance having a first phase component and a first magnitude component; and producing an indicator of the second location as a function of the first phase component;

the step of detecting a complex impedance between the first and second locations comprising the steps of:

detecting a first impedance at a first frequency; and detecting a second impedance at a second frequency different from the first frequency, wherein the first phase component corresponds to the first impedance and a second phase component corresponds to the second impedance.

9. The method of claim 8, further including the step of comparing the indicator to a reference indicator to determine if the second location is the apical location.

10. The method of claim 8 wherein the step of producing an indicator as a function of the first phase component further includes producing the indicator as a function of the first magnitude component.

11. The method of claim 8 wherein the step of producing an indicator as a function of the first phase component comprises producing a first test score as a function of the first and second phase components.

12. The method of claim 11 wherein the first test score is also a function of the magnitudes of the first and second impedances.

13. The method of claim 11, further including the step of producing a second test score as a function of the magnitudes of the first and second impedances.

14. The method of claim 8, further including the step of displaying the first test score on a display configured for viewing by a user.

15. The method of claim 14 wherein the step of displaying the first test score on a display configured for viewing by a user including displaying the first test score as a bar graph.

16. The method of claim 8 wherein the step of detecting a complex impedance between the first and second locations comprises the steps of:

producing a multifrequency testing signal having spectral components at each of the first and second frequencies;

applying the multifrequency signal to the patient;

detecting a response signal produced by the multifrequency signal; and extracting the spectral components of the response signal at the first and second frequencies.

17. A method of indicating apical position, comprising the steps of:

probing a root canal with a probe; detecting a complex component of a complex impedance between the probe and a location on a patient's body;

producing a first test score as a function of the complex component; and displaying the first test score to a user; and producing a second test score indicating testing conditions based upon a selected component of the complex impedance; and producing a visible indication of the testing conditions in response to the second test score.

18. The method of claim 17 wherein the step of displaying the first test score comprises activating a bar graph indicator.

19. The method of claim 17 wherein the step of providing a visible indication of the testing conditions includes activating a second bar graph.

20. A method of indicating apical position, comprising the steps of:
    probing a root canal with a probe;
    detecting a complex component of a complex impedance between the probe and a location on a patient's body;
    producing a first test score as a function of the complex component;
    displaying the first test score to a user;
    identifying undesirable measuring conditions in response to a selected component of the complex impedance; and
    providing an audible indication of the undesirable measuring conditions.

21. A method of determining a probe location, comprising the steps of:
    applying the probe to a patient's body;
    applying a multifrequency signal to the probe, the multifrequency signal having spectral components at a plurality of more than two frequencies;
    detecting a response signal produced in response to the applied multifrequency signal;
    extracting more than two selected spectral components of the response signal; and
    in response to the extracted spectral components, producing an output indicating the probe location based on a sum of amplitude ratios and of phase angles of the extracted spectral components.

22. The method of claim 21 wherein the output is a test score.

23. The method of claim 21, further comprising the steps of:
    comparing the extracted spectral components to a reference set of spectral components corresponding to the probe being positioned at a desired location; and
    when the extracted spectral components match the reference spectral components, indicating that the probe is positioned at the desired location.

24. The method of claim 23 wherein the step of extracting selected spectral components from the response signal includes heterodyning the response signal with signals at frequencies of the selected spectral components.

25. The method of claim 21 wherein the step of extracting selected spectral components of the response signal comprises operating on the response signal with a transform technique.

26. The method of claim 25 wherein the transform technique is a Fast-Fourier Transform.

27. The method of claim 21 wherein the step of producing the output includes the step of:
    producing the output based on a sum of amplitude ratios and of phase angles of the extracted spectral components that are higher for higher frequency components than for lower frequency components.

28. The method of claim 21 wherein:
    the step of applying a multifrequency signal to a probe includes the step of applying a multifrequency signal having spectral components at a plurality of at least five frequencies;
    the extracting step includes the step of extracting at least five selected spectral components of the response signal; and
    the producing step includes the step of producing the output based on a sum of amplitude ratios and of phase angles of the lowest frequency extracted spectral component to the other frequency extracted spectral components.

29. The method of claim 21 wherein:
    the step of applying a multifrequency signal to a probe includes the step of applying a multifrequency signal having spectral components that are double the frequency of a lower frequency component; and
    the step of extracting selected spectral components of the response signal comprises operating on the response signal with a Fast-Fourier Transform technique.

30. The method of claim 21 wherein:
    the step of producing the output includes producing an output based on a sum of amplitudes of extracted spectral components.

31. The method of claim 21 wherein:
    the step of applying the multifrequency signal to the probe includes applying a multifrequency signal having spectral components at a plurality of more than two frequencies in the range of from 500 Hz to 10 kHz.

32. The method of claim 21 wherein:
    the step of applying the multifrequency signal to the probe includes applying a multifrequency signal having spectral components at a plurality of more than two frequencies selected from the group consisting of 500 Hz, 1 kHz, 2 kHz, 4 kHz and 8 kHz.

* * * * *